United States Patent

Hurme et al.

Patent Number: 6,054,119
Date of Patent: Apr. 25, 2000

[54] PREPARATION USED IN DENTAL CARE

[76] Inventors: Tapio Hurme, Puolalanpuisto 3 A 1, FIN-20100 Turku; Martti Neva, Humalistonkatu 17 a A 28, FIN-20100 Turku; Kimmo Leskinen, Nuolenkuja 3, PL 13, FIN-21420 Lieto, all of Finland

[21] Appl. No.: 09/000,365

[22] PCT Filed: Jul. 26, 1996

[86] PCT No.: PCT/FI96/00423

§ 371 Date: Mar. 27, 1998

§ 102(e) Date: Mar. 27, 1998

[87] PCT Pub. No.: WO97/04741

PCT Pub. Date: Feb. 13, 1997

[30] Foreign Application Priority Data

Jul. 28, 1995 [FI] Finland ..................... 953634

[51] Int. Cl.[7] .............. A61K 7/16; A61K 7/18; A61K 9/20; A61K 9/48

[52] U.S. Cl. .............. 424/52; 424/48; 424/49; 424/57; 424/435; 424/440

[58] Field of Search .............. 424/48, 435, 440, 424/49–58

[56] References Cited

U.S. PATENT DOCUMENTS

| | | |
|---|---|---|
| 3,914,434 | 10/1975 | Bohni ........................ 424/49 |
| 4,153,732 | 5/1979 | Muhler et al. ............... 424/49 |
| 4,170,632 | 10/1979 | Knocht et al. .............. 424/48 |
| 4,726,943 | 2/1988 | Klueppel et al. ........... 424/49 |
| 4,978,521 | 12/1990 | Blue . |
| 5,089,255 | 2/1992 | Gaffar et al. ............... 424/52 |
| 5,378,131 | 1/1995 | Greenberg ................. 424/440 |
| 5,470,566 | 11/1995 | Lutzen ....................... 424/49 |
| 5,496,541 | 3/1996 | Cutler et al. . |
| 5,645,853 | 7/1997 | Winston et al. ........... 424/446 |
| 5,688,491 | 11/1997 | Shahidi ...................... 424/49 |

FOREIGN PATENT DOCUMENTS

| | | |
|---|---|---|
| 0 309 414 | 3/1989 | European Pat. Off. . |
| 0 414 932 | 3/1991 | European Pat. Off. . |
| 41 23 450 | 1/1993 | Germany . |

*Primary Examiner*—Shep K. Rose
*Attorney, Agent, or Firm*—Kubovcik & Kubovcik

[57] ABSTRACT

A preparation used in dental care to protect the teeth, which preparation is anhydrous, with the possible exception of crystal water, and by structure, for example a powder, solid tablet or other anhydrous compositions. The preparation contains a remineralising component. pH buffer component, xylitol and fluoride. Due to the effect of the water contained in the saliva or water added otherwise, the compounds in the preparation react with each other so as to bring about both a remineralisation reaction correcting cavity formation in the teeth, and a pH buffering reaction prevention cavity formation in the teeth.

16 Claims, No Drawings

PREPARATION USED IN DENTAL CARE

The object of the invention is a preparation used in dental care.

Problems relating to teeth are caused by cavity formation, or caries, and chemical dissolution caused by acids, or erosion. These continue to be a major health problem also among adults. Due to various factors, caries in particular is increasingly a problem for the ageing adult population who still have their own teeth. Such factors include impaired motor coordination, lack of motivation, reduced salivary secretion, use of medication or general ill health.

In simple terms, caries and erosion represent a change in the equilibrium state between demineralisation and remineralisation, towards demineralisation. The oral remineralising capacity is maintained by the saliva, particularly the calcium and phosphate contained in the saliva and the buffering capacity of the saliva.

According to present knowledge, the importance of fluoride used in dental care lies in the stimulation of remineralisation. Remineralisation occurs in the mouth daily, for example, always after a meal, due to the effect of the saliva. Even small repeated fluoride concentrations in the mouth are advantageous, because in the presence of fluoride, the apatite crystals apposited on the hard tissue of the tooth are more resistent to acids and more regular in structure than those formed without fluoride.

Xylitol, another substance used in dental care, has many good properties. Firstly, it does not form organic acids harmful to the teeth through the action of bacteria. Being a sweet substance, it stimulates salivary secretion, which means that the calcium, phosphate and bicarbonate concentrations in the saliva increase. Xylitol also reduces the amount of the most detrimental caries bacteria, such as the so-called mutans streptococci, on the surface of the teeth. Calcium and phosphate are essential ingredients of the saliva, as saliva contains useful calcium and phosphate salts in soluble, supersaturated form. They may either be precipitated onto the surface of the teeth during remineralisation or they may form calculus above the gums.

A useful and important property of saliva is its buffering ability, or buffer capacity. A high and good buffer capacity prevents the detrimental demineralisation effects caused to the hard issue of the dentition by both caries arising from acids produced by bacteria, and by erosion caused, for example, by the acids in food. The buffer capacity of saliva follows primarily from its bicarbonate content.

In patients with reduced salivary secretion, the natural defence mechanisms of the saliva have deteriorated, including its remineralising capacity. These patients are particularly prone to all hard tissue damage to the dentition, particularly to caries. For this reason, for example, rinsing with fluoride and so-called remineralisation solutions have already for many years been recommended to hyposalivation patients, in order to increase the resistance of the teeth. The use of xylitol has also been recommended. The problem is that all these preparations are separate. No easy-to-use and effective preparation is known which contains even most of the agents favourable to the health of the dentition.

Attempts have, however, been made to combine several of the above-mentioned agents into one preparation. One such preparation is a lozenge presented by the researchers Nilner, Vassilakos and Birkhed (Nilner K, Vassilakos N, Birkhed D. Effect of buffering sugar-free lozenge on intraoral pH and electrochemical action. Acta Odontol Scand. 1991:49: 267–272). The preparation contains 43.8% of xylitol and 42.3% of sorbitol. In total, the proportion of these sugar alcohols, which are present in a ratio of approximately 1:1 is thus 86.1%. The buffering compounds in this preparation are sodium bicarbonate (3.0%), sodium hydrogen phosphate (3.2%), disodium hydrogen phosphate (3.3%), and sodium: polyphosphate (1.2%). The proportion of these sodium salt buffers in the total weight of the preparation is thus 10.6%.

This formulation also contains 0.77% of carboxymethylcellulose as a binder, and the usual amount, that is, 1.38% of magnesium stearate, known as an additive in tabletting. The formulation also contains 0.92% of mint aroma as flavouring and small amounts of non-buffering salts, such as 0.17% of calcium chloride and 0.015% of zinc chloride. The researchers explain that the buffering effect of the formulation is based on the bicarbonate phosphate buffer.

The above-mentioned formulation has been shown to clearly increase the salivary buffer capacity. The greatest disadvantage of the preparation is, however, the complete lack of fluoride. Correspondingly, the proportion of calcium is also extremely small, because 0.17% of salt contains only 0.061% of calcium. In other words, one 650 mg lozenge contains only 0.40 mg of calcium.

Due to the above, this formulation does not enable the formation of fluoride apatite. The formation of hydroxyapatite bears no practical importance due to the insignificantly small amount of calcium. Thus, the formulation has no real significance for remineralisation. The study does not, however, provide any explanation or reveal the significance of the small amount of calcium present in the preparation.

In other known preparations, fluoride has been added to the lozenges in addition to xylitol. However, these preparations do not contain buffering compounds, which would increase the salivary buffer capacity. Similar formulations also appear in toothpastes, which are in the physical state of a paste and contain water. There is, for example, a toothpaste which contains bicarbonate and sodium fluoride.

The aim of the present invention is to eliminate the foregoing problems and to provide a new preparation which does not have the above-mentioned disadvantages. It is characteristic of the preparation relating to the invention that the preparation is anhydrous, with the possible exception of crystal water, and by structure, for example a powder, solid tablet or other anhydrous composition, that the preparation contains a remineralising component and a pH buffer component, and that due to the effect of the water contained in the saliva or water added otherwise, the compounds in the preparation react with each other so as to bring about both a remineralisation reaction, correcting cavity formation in the teeth, and a pH buffering reaction preventing cavity formation in the teeth.

In addition to the effect of increasing salivary secretion, the preparation relating to the invention also has a more efficient buffer effect, and at the same time (in situ) a remineralising effect taking place through chemical reactions, by means of hydroxyapatite and fluoride apatite. The preparation relating to the invention is intended, above all, to compensate for the small amount of remineralising agents in the mouth of hyposalivation patients.

The preparation relating to the invention provides the following advantages with respect to earlier formulations:

Remineralisation takes place already in the mouth (in situ) and the fluoride dosed is bound in a useful form.

The other potential side effects of excess free fluoride are minimised.

The potential of remineralisation is markedly greater as compared with earlier preparations.

Due to the chemical reaction, the correct concentrations of buffering components are in exactly the correct chemical equilibrium ratio, that is, such as are characteristic of the surface-chemical interaction of the hard tissue.

The ingredients do not cause chemical corrosion.

The substances relating to the invention are known and acceptable as such. The combination relating to the invention also keeps well and does not contain easily fermenting components. The product increases salivary secretion, thus promoting chemical reactions for which the presence of water is essential. In a dry state, there is no reaction in the product.

The ingredients in the formulation relating to the invention have a buffering effect both before and after the chemical reaction. The reaction temperatures are, however, such that they have no significance on the temperature of the saliva.

Preferred embodiments of the invention are:

An inorganic or organic calcium compound having buffer capacity, e.g. (hydrogen) carbonate, carbonate, acetate, propionate, sorbate, ascorbate, aspartate, lysinate, gluconate, or lactate. Of these, the most advantageous economically is inorganic carbonate.

An alkali metal compound having buffering capacity in addition to the above calcium compounds. Such compounds are phosphates, pyrophosphates, polyphosphates and hydrogen phosphates. Of these, the most advantageous are different sodium and potassium phosphates and hydrogen carbonates, particularly disodium hydrogen phosphate.

An alkali metal fluoride, preferably sodium or potassium fluoride. Fluoride may also be bound in the same compound as phosphate, for example in the form of sodium monofluorophosphate.

According to a preferred embodiment of the invention, a dry compressed preparation, such as a tablet, is formed of the ingredients together with xylitol, which stimulates salivary secretion, the tablet containing the buffer compounds which participate in the chemical reaction, such as calcium, alkali metal, phosphate and fluoride compounds.

When the tablet relating to the invention comes into contact with water, or preferably with the saliva, the buffering effect is created immediately as the tablet disintegrates. With water as a medium, thermodynamically advantageous reactions take place between the compounds, the reactions settling into a state of equilibrium in the ambient condition. At the same time, new water-soluble buffering compounds are formed.

As a final result of the chemical reactions, either fluoride apatite or hydroxyapatite, or both, are formed of compounds characteristic of the invention, calcium, phosphates and fluoride. These are all structural substances essential to the hard tissue of the tooth.

The preparation relating to the invention differs from all other preparations in that the chemical reactions take place due to the effect of the saliva, while new buffer compounds resisting pH changes are at the same time formed from the starting materials.

EXAMPLE 1

The example shows a preferred formulation and the changes it effects on the properties of the saliva and on the formation of remineralising components. The example discloses a preparation in the form of a tablet, with the following formulation:

| Ingredient | proportion, % | amount, mg |
|---|---|---|
| Xylitol | 68.73 | 350 |
| Calcium carbonate | 14.02 | 71 |
| Disodium hydrogen phosphate | 10.92 | 55 |
| Zinc ascorbate | 4.36 | 22 |
| Sodium fluoride | 0.11 | 0.5 |
| Magnesium stearate | 0.98 | 5 |
| Silicon dioxide (Aerosil) | 0.39 | 2 |
| Menthol | 0.49 | 2.5 |
| Total | 100.00% | 508.0mg |

The purpose of the xylitol is to increase salivary secretion and to give the tablet a sweet taste. On the other hand, xylitol is known to form a weak complex with a calcium ion, which facilitates the absorption of calcium in the digestive system, in as far as calcium is not involved in situ in the chemical reaction to form apatites.

The reactive components in the formulation are calcium carbonate, disodium hydrogen phosphate and sodium fluoride. The amount of sodium fluoride has been selected so that a dose of three tablets per day will not exceed the amount which represents the minimum limit of a prescribed drug. The amount of fluoride may obviously be greater.

The purpose of the zinc ascorbate is both to act as a microbicide and to regulate the redox potential. A dose of three tablets per day also ensures the sufficient intake of zinc and vitamin C.

Magnesium stearate is an additive (slip agent) in tabletting. Menthol acts as a component providing a fresh taste. The purpose of the silicon dioxide is to act as an anti-caking agent.

A clinical experiment was carried out with the tablet, in which the effect of the tablet on salivary properties was tested in 20 subjects, both immediately and after one month's use. Three tablets were taken daily.

The immediate effect was analysed by collecting a so-called whole saliva sample immediately before chewing the tablet and two, five, 10 and 20 minutes after chewing had been completed. The salivary flow rate was measured at each observation point. Salivary pH and buffer capacity were measured immediately after collection. The saliva samples were frozen to −20° C. and subsequently analysed for calcium, inorganic phosphate and fluoride. Calcium was assayed using an atomic absorption spectrometer, phosphate was assayed chemically and fluoride electrometrically using a fluoride electrode.

The salivary flow rate was observed to increase by 35–40% immediately at the onset of sucking. After one month's use, the tablet had the same effect, but long-term use did not increase the salivary flow rate statistically compared with the baseline situation. The stimulation of the salivary flow rate was, therefore, due to the property of the tablet when sucking it, but it did not bring about any permanent change in salivary secretion in persons who already had normal salivary secretion.

The salivary pH increased (baseline pH was 6.8–6.9) statistically significantly to a peak value of 7.3–7.4 immediately at the onset of sucking the tablet and remained remarkably high for at least 20 minutes (pH over 7.15). After one month's use, the baseline pH values had not changed, which means that the change in pH was due to the effect of the tablet. Salivary pH remained clearly in the alkaline range even after 20 minutes from onset of sucking the tablet (pH range 7–7.5).

The buffer capacity of saliva increased statistically significantly for at least 10 minutes from the onset of sucking the tablet. The same effect also appeared after one month's continuous use each time a tablet was taken.

At the onset of sucking the tablet the fluoride, calcium and phosphate concentrations of the saliva changed as a function of time. The fluoride concentration reached its highest value (6–7 ppm) within about two minutes from the onset of sucking. The average concentration of calcium in the saliva reached its highest value within about 2–4 minutes (50 µg/ml). The phosphorus content of saliva also reached its highest value (approx. 325 µg/ml) within 2–4 minutes. After about twenty minutes from the onset of sucking, the concentrations returned to the baseline.

The analysis of the samples showed apatite formation in situ, which means that reactions had taken place.

EXAMPLE 2

This example illustrates a variation of the formulation in another preparation and utilises organic calcium salt. The preparation was made into a tablet-form, liquorice-flavoured pastille preparation, with the following formulation:

| Ingredient | proportion, % | amount, mg |
|---|---|---|
| Xylitol | 67.70 | 350 |
| Calcium acetate | 21.66 | 112 |
| Dipotassium hydrogen phosphate | 7.35 | 38 |
| Zinc oxide | 1.16 | 6 |
| Potassium fluoride | 0.13 | 0.7 |
| Liquorice root powder | 1.99 | 10.3 |
| Total | 100.00% | 517.0mg |

Calcium acetate was selected from the organic, easily soluble calcium salts having buffer capacity as the starting material. As an aqueous solution, calcium acetate is slightly alkaline (pH 7.6).

Dipotassium hydrogen phosphate is an example of another alkali metal salt which can be used. The purpose of zinc oxide is to act in the mouth so as to prevent the growth of microbes, and on the other hand it is slightly alkaline in its reaction with water. The purpose of liquorice root is to give a pleasant taste to the otherwise soluble, salt-like ingredients.

The pastille-form preparation was tested as above. The increase in pH was not quite as good, but thanks to its said solubility, the increase in pH was steeper than in the previous example. The buffer capacity was also sufficiently good.

A sample taken from the mouth revealed the apatites necessary for remineralisation, which were formed as a result of chemical reactions. The quantitative amount of apatites in the saliva was greater, because the solubility of the calcium compound was not a factor restricting reaction rate as in example 1.

EXAMPLE 3

This example describes the formulation of a chewing gum preparation.

| Ingredient | proportion, % | amount, mg |
|---|---|---|
| Xylitol | 63.63 | 350 |
| Calcium carbonate | 12.82 | 70.5 |
| Calcium acetate | 9.09 | 50 |
| Calcium ascorbate | 4.18 | 23 |
| Disodium hydrogen phosphate | 10.18 | 56 |
| Sodium fluoride | 0.09 | 0.5 |
| Total | 100.00% | 550.0mg |

The preliminary composition relating to this formulation was used to prepare chewing gum. Additional ingredients were so-called gum base, natural flavourings, e.g. spearmint oil, thickeners (E414), stabilisers (E322, E471), glazing agents (E901, E903, E904) and as a sweetener, acesulphame K (E950), in addition to xylitol. These components merely contributed to the physical form and enjoyability of the preparation.

Calcium acetate was selected as a slightly alkaline buffer compound. In addition to being a source of vitamin C, calcium ascorbate acts as a source of soluble calcium for apatite formation. Calcium ascorbate is also water-soluble and acts as a buffer within the neutral and slightly alkaline pH range (pH 6.8–7.4). The preparation relating to the invention may consist of several of the starting materials which participate in the reaction.

The salivary pH increased rapidly as in the previous example, and reached the level of 7.6. The buffer capacity was assessed using a Dentobuff Strip indicator, according to which the buffer capacity was on average good or excellent. The effect of the chewing gum lasted for an average of 15–20 minutes. In a sample taken from the mouth, the formation of apatites was shown both chemically and e.g. using an X-ray crystallographer.

The traditional way to remove dental plaque or stains has been cleaning with the aid of a rubber cup or brush, performed in the dental office by the dentist or dental hygienist. The cleaning paste usually contains pumice or other type of rubbing particles dissolved in water. Some cleaning pastes also contain small amounts of fluoride. One of the recently launched methods is to use baking soda as an ingredient in a high-pressure spray applied onto tooth surfaces. After cleaning, the small particles can be easily removed by a suction pipe connected to the dental unit. So far, however, all commercially available machines only remove stains or plaque but have no therapeutic or preventive action against dental caries.

The new dental product according to the application is applicable to both cleaning methods mentioned above but it's great advantage is that by comprising fluoride, xylitol and other remineralizing agents it can also restore the microscopical damages induced by cleaning as well as simultaneously to depress the microbial activity due to the presence of fluoride and xylitol. Both as a powder in a spray form or as a paste it would be close to ideal since the cleaning properties can be changed by changing the particle size without loosing the anticariogenic or even therapeutic activity of the new product.

EXAMPLE 4

This example describes a powder formulation:

| Component | relative amount, % | amount, mg |
|---|---|---|
| Xylitol | 35.55 | 7110 |
| Calcium carbonate | 35.50 | 7100 |
| Disodium hydrogen phosphate | 27.75 | 5550 |
| Sodium fluoride | 0.0075 | 1.50 |
| Silica dioxide (Aerosil) | 1.00 | 200 |
| Menthol | 0.20 | 40 |
| Total | 100.0% | 20001.5 mg |

The used components are chemically same as in the example 1. Magnesium stearate is not used in this example because it is tableting aid and this example describes powder-like formulation.

The relative amounts are also different, but contain characteristic components of the innovation:

xylitol and fluoride-compound, which promote remineralisation and inhibit the action of microbes compounds for remineralisation and basic buffer containing calcium and phosphates The amount of fluoride is relatively smaller only because the total dose of powder is about 10 grams during one application. The dose of fluoride should be within safe limits.

All the above mentioned single components were air-grounded before mixing. Silica dioxide was not grounded, because it was fine powdered. The Function of silica dioxide is anti-caking and fee-flowing agent. The grounded and dry components were mixed to form a homogeneous mixture, which had the following particle distribution:

80% less than 20 $\mu$m

18% within the area of 20–50 $\mu$m

2% within the area of 50–75 $\mu$m

The most abundant amount of particles had size of 10–15 $\mu$m.

The mixture was applied into a mouth with the aid of air-blow equipment, which is commonly used to clean teeth and to remove stains from the surface of teeth. The fine powdered components are air-blown through the nozzle with high speed. Water is added into the powder in the nozzle. The suspension of powder and water is injected to the surface of teeth with the aid of pressure.

Immediately after the treatment of teeth the pH of saliva was measured to be 7.4. The concentrations of fluoride, calcium and phosphorus in saliva were measured: fluoride 3 ppm, calcium 50 $\mu$g/ml and phosphorus 320 $\mu$g/ml. The observed concentrations were about the same as in the example 1, except in the case of fluoride.

The analysis of samples show, that hydroxyfluorapatite and apatite were formed.

It is obvious to a person skilled in the art that the invention is not limited merely to the cases presented in the examples, but that there is a great number of possible combinations which fall within the scope of the invention defined in the claims. The tablet relating to the invention may obviously also contain other additives affecting either the technical properties, enjoyability or redox potential of the preparation. To an expert it as also obvious that the preparation relating to the invention may be, for example, in compressed form, such as a tablet, capsule, lozenge or chewing gum. The external appearance of the preparation may thus be selected freely.

We claim:

1. An anhydrous preparation used in dental care, consisting essentially of:

a) an organic or inorganic calcium compound having buffering capacity, b) an alkali metal phosphate, c) an alkali metal fluoride, and d) xylitol in amounts such that, due to the effect of water contained in saliva or water added otherwise, said components (a), (b) and (c) in the preparation react with each other so as to bring about a remineralisation reaction correcting cavity formation in teeth and an alkaline pH buffering reaction preventing cavity formation in teeth, and that said prepreparation causes an effect of stimulating salivary secretion.

2. A preparation as claimed in claim 1, wherein the preparation is in a compressed form selected from the group consisting of a tablet, capsule, lozenge and chewing gum.

3. A preparation as claimed in claim 1, wherein, due to the effect of water or saliva, said preparation forms a remineralising ingredient containing at least one phosphate and/or fluoride compound, which is present as an alkali metal salt.

4. A preparation as claimed in claim 1, wherein the remineralising ingredient is hydroxyapatite and/or fluoride apatite.

5. A preparation as claimed in claim 1, wherein the remineralising ingredient is an alkali metal fluoride.

6. A preparation as claimed in claim 1, wherein said alkali metal phosphate and said alkali metal fluoride are contained in said preparation as the compound sodium monofluorophosphate.

7. A preparation as claimed in claim 1, wherein said calcium compound is a carbonate or organic calcium salt.

8. A preparation as claimed in claim 1, wherein said inorganic or organic calcium compound having buffering capacity is a carbonate, hydrogen carbonate, acetate, propionate, sorbate, ascorbate, aspartate, lysinate, gluconate, or lactate.

9. A preparation as claimed in claim 1, wherein said alkali metal phosphate is selected from the group consisting of phosphate, pyrophosphate, polyphosphate, and hydrogen phosphate.

10. A preparation as claimed in any of the claim 1, wherein the preparation is a dry tablet which disintegrates on coming into contact with saliva.

11. A preparation as claimed in claim 1, wherein the preparation is a tablet containing the following ingredients: xylitol, calcium carbonate, disodium hydrogen phosphate, zinc ascorbate, sodium fluoride, magnesium stearate, silicon dioxide (Aerosil) and menthol.

12. A preparation as claimed in claim 1, wherein the preparation is a tablet containing the following ingredients: xylitol, calcium acetate, dipotassium hydrogen phosphate, zinc oxide, potassium fluoride and liquorice root powder.

13. A preparation as claimed in claim 1, wherein the preparation is a tablet containing the following ingredients: xylitol, calcium carbonate, calcium acetate, calcium ascorbate, disodium hydrogen phosphate and sodium fluoride.

14. A preparation as claimed in claim 1, wherein the preparation contains more than 0.1% of calcium in order to bring about remineralisation.

15. A preparation as claimed in claim 5, wherein said alkali metal fluoride is selected from sodium fluoride, potassium fluoride and mixtures thereof.

16. A preparation as claimed in claim 15, wherein the preparation contains more than 1% of calcium.

* * * * *